United States Patent [19]

Koide et al.

[11] Patent Number: 4,483,846
[45] Date of Patent: Nov. 20, 1984

[54] LONG-LASTING THREE-LAYERED PHARMACEUTICAL FILM PREPARATIONS

[75] Inventors: Tatsushi Koide, Yawata; Seiei Sasatani, Matsubara; Kohji Inaba, Neyagawa, all of Japan

[73] Assignee: Ono Pharmaceutical Co., Ltd., Kyoto, Japan

[21] Appl. No.: 464,174

[22] Filed: Feb. 7, 1983

[30] Foreign Application Priority Data

Feb. 5, 1982 [JP] Japan .................................. 57-16331

[51] Int. Cl.³ ...................... A01N 25/26; A01N 25/34
[52] U.S. Cl. ........................................ 424/19; 424/16;
424/21; 424/28; 604/890; 604/892; 604/896;
604/897
[58] Field of Search ........................ 424/16, 19, 21, 28;
604/890, 892, 896, 897

[56] References Cited

U.S. PATENT DOCUMENTS

| | | | |
|---|---|---|---|
| 3,926,188 | 12/1975 | Baker et al. | 128/260 |
| 4,180,558 | 12/1979 | Goldberg et al. | 424/16 |
| 4,317,447 | 3/1982 | Williams | 128/260 |
| 4,335,097 | 6/1982 | David et al. | 424/19 X |
| 4,359,483 | 11/1982 | Kaetsu et al. | 427/2 |
| 4,451,260 | 5/1984 | Mitra | 604/890 |

OTHER PUBLICATIONS

Derwent, No. 47633v.
Derwent, No. 35619e.
Derwent, No. 43052w.
Chem. Abs.; 91: 112398w (Khristenko et al.).

Primary Examiner—Esther M. Kepplinger
Assistant Examiner—Shawn P. Foley
Attorney, Agent, or Firm—Sughrue, Mion, Zinn, Macpeak, and Seas

[57] ABSTRACT

The present invention provides new three-layered pharmaceutical film preparations which comprise one drug-storing middle layer composed of one or more (a) polyvinylpyrrolidone, (b) hydroxypropyl cellulose, (c) plasticizers and (d) organic acids, containing prostaglandin analogues, and two release-controlling layers on both sides of the said middle layer, composed of one or more (a) hydroxypropyl cellulose and (b) plasticizers, containing or not containing prostaglandin analogues, and which may release the drug at the desired concentration lastingly for an extended period of time, with great high biological availability, and can make this release "zero-order release", and further have improved the stability of the drug contained therein, and in which the form of the preparation is not retained at the administered site after administration.

10 Claims, 1 Drawing Figure

PERCENT DISSOLUTION (%)
IN VARIOUS PREPARATIONS

●——● : HPC FILM (COMPARISON)
○——○ : N-HP FILM (COMPARISON)
■——■ : L-HP FILM-(1) (INVENTION)
□——□ : L-HP FILM-(3) (INVENTION)

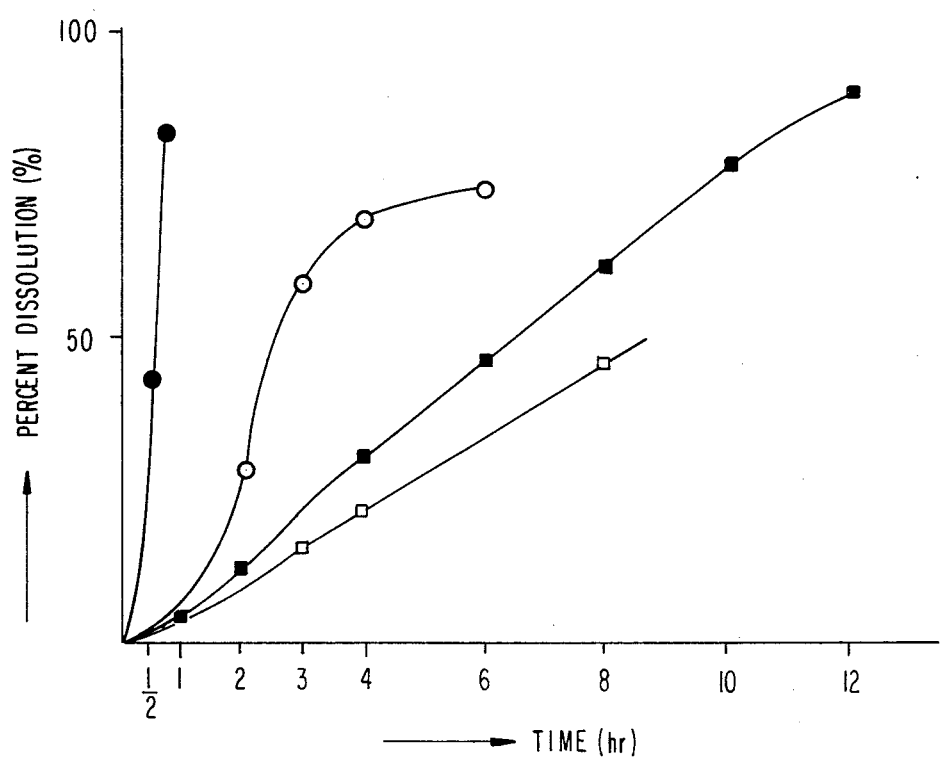

LONG-LASTING THREE-LAYERED PHARMACEUTICAL FILM PREPARATIONS

BACKGROUND OF THE INVENTION

1. Field of the Invention

This invention relates to novel three-layered pharmaceutical film preparations and processes for the production thereof. More specifically, this invention relates to the three-layered pharmaceutical film preparations which comprise one drug-storing middle layer composed of water soluble polymers and therapeutically active ingredients (prostaglandin analogues), and two release-controlling layers on both sides of the said middle layer, composed of water soluble polymers, characterized by that the prostaglandin analogues contained therein exhibit the desired long-lasting release pattern, further fully satisfying the purpose that drug preparations which have very high biological availability and are effective and safe should be supplied, as well as the novel processes for production thereof.

2. Description of the Prior Art

Various techniques for releasing drug for an extended period of time have heretofore been reported in the literature. For instance, there are known coating methods to maintain release for an extended period of time, as found mainly in oral tablets, intravaginally devices, drug release devices utilizing the osmotic pressure and dispensers utilizing semipermeable membranes or porous membranes etc. In more recent years, there have also been reported the development of polymers for achieving long-lasting release intended for topical applications, long-lasting films and containers for releasing the drug quantitatively by release from one side; in any case, however, they have disadvantages that high levels of techniques and equipment are required and that the form of that device (preparation) is retained even in the vital body (administration site) to give an extraneous feel to the human. Further, they also have such disadvantages that the expected drug efficacy is difficult to obtain because the stability of the active ingredient is adversely affected, the biological availability is low and the like. As a method eliminated these disadvantages, there are film preparations and preparations like cellulose fiber to obtain long-lasting release by using cellulose ether etc. soluble in body fluid (see Japanese Patent Kokai No. 49-133519, Derwent No. 47633V). Although the form of the said preparations is not retained in the administration site, they have disadvantages that high levels of techniques and equipment, and further high temperature in the production process are required, and, therefore, it is considered that the stability of the active ingredient is adversely affected by high temperature in case of the production of the preparation containing prostaglandin analogues.

In more recent years, we have proposed milti-layered pharmaceutical film preparations which comprise water soluble polymer bases and water insoluble polymer bases, for the purpose of maintaining the release of a drug for an extended period of time (see Japanese Patent Kokai No. 57-70816, Derwent No. 35619E). However, though these pharmaceutical film preparations are improved, they still have disadvantages that the biological availability is not sufficient, the lasting time of release is short, and the release tends to be "sigmoid release" (S-shaped release) and the like. Therefore, it can not be said that they are satisfactory film preparations.

On the other hand, there are known several methods for the production of a film using hydroxypropyl cellulose (abbreviated HPC hereafter). That is to say, as a process for the production of the films using HPC, there are known a process dissolving HPC in a suitable organic solvent and then evaporating the solvent, and a process dissolving HPC in water and then evaporating water (see Japanese Patent Kokai No. 56-36173, Derwent No. 43052W). The said processes are very useful when HPC used has relatively small molecular weight, e.g. 30,000–150,000 and low viscosity. However, there is a possibility to produce various problems when HPC used has the molecular weight of 250,000–400,000 and high viscosity.

For example, practically speaking, the upper limit of the solubility of HPC having the molecular weight of 250,000–400,000 (abbreviated HPC—H hereafter) in water or methanol is 4% and, therefore, a HPC—H solution having a thickness of 1 mm becomes the HPC—H film having a thickness of only about 0.04 mm after evaporation. Accordingly, it is necessary to pour out a HPC—H solution having a thickness of about 7.5 mm in order to obtain a HPC—H film having a thickness of 0.3 mm which is preferable thickness for the release-controlling layers in the pharmaceutical film preparation of the present invention. However, the increase of a volume of the solvent used causes various problems that a film having uniform thickness can not be obtained, that it takes a lot of time to dry the film, that it is difficult to dry completely, and further, that the environment in or out of the laboratory is polluted and the like. Particularly, it is presumed that the difficulty in removing bubbles owing to its high viscosity becomes a large obstacle to the mass production.

SUMMARY OF THE INVENTION

Accordingly, an object of the present invention is to provide new three-layered pharmaceutical film preparations which have eliminated the disadvantages of the conventional techniques, that is, which may release the drug at the desired concentration lastingly for an extended period of time, with great high biological availability, and can make this release "zero-order release" (straight-line release), and further have improved the stability of the prostaglandin analogues contained therein, and in which the form of the preparation is not retained at the administered site (in the vagina) after administration.

Furthermore, another main object of the present invention is to provide processes for the production of the pharmaceutical film preparations of the present invention, in particular new processes for the production of release-controlling layers in the said film preparations using HPC—H. That is to say, the present invention is also provides new processes for the production of the HPC—H film having a suitable thickness by using a small amount of solvent.

BRIEF DESCRIPTION OF THE DRAWING

In the drawing:
The FIGURE is a graph showing the percent dissolution of the drug in various preparations.

DETAILED DESCRIPTION OF THE INVENTION

The present invention provides three-layered pharmaceutical film preparations which comprise one drug-storing middle layer containing therapeutically active ingredients, and two release-controlling layers on both sides of the said middle layer, controlling the release of the drug. The size is preferable such that the surface area (the sum of the surface areas of the release-controlling layers on the both sides) is 2–20 cm$^2$ and the thickness is 0.3–3.0 mm, especially the size of 5–15 cm$^2$ in surface area and 0.6–1.5 mm in thickness being desired.

The drug-storing middle layers in the pharmaceutical film preparations of the present invention, are composed of one or more (a) polyvinylpyrrolidone (abbreviated PVP hereafter), (b) HPC, (c) plasticizers and (d) organic acids and contain required amounts of the drug.

Various standardized PVP are commercially available, according to its molecular weights. For example, Kollidon-17 (molecular weight; ca. 11,500), Kollidon-30 (molecular weight; ca. 40,000) and Kollidon-90 (molecular weight; ca. 360,000) (All is registered Trade Mark and prepared by BASF A.G.) etc. are on the market. Any standardized PVP mentioned above or the combination of two or more of them may be used as the drug-storing middle layer, and PVP having the molecular weight of 300,000–400,000 is preferred. Kollidon-90 is more preferred.

Various standardized HPC are also commercially available, according to its molecular weights. For example, besides HPC—H hereinbefore mentioned, HPC—M (molecular weight; 110,000–150,000), HPC—L (molecular weight; 55,000–70,000) and HPC—SL (molecular weight; 30,000–50,000) (All is registered Trade Mark and prepared by Nippon Soda K.K.) etc. are on the market. Any standardized HPC mentioned above or the combination of two or more of them may be used as the drug-storing middle layer, and HPC—H is preferred. The amount of HPC to be added is preferably such that it is added to the drug-storing middle layer at a proportion of 5–30% by weight, more preferably 5–10%.

The plasticizers used in the drug-storing middle layer, include biologically inactive, conventional plasticizers, for example, propylene glycol, glycerol, polyethylene glycol and lauryl alcohol, or the combination of two or more of them, preferably polyethylene glycol or lauryl alcohol. Since the plasticizers make the films more flexible, a physical difficulty in the administration site may be prevented. The amount of the plasticizer to be added is preferably such that it is added to the drug-storing middle layer at a proportion of 10–40% by weight, more preferably 25–35% by weight.

The prostaglandin analogues in the drug-storing middle layer include prostaglandin F compounds and prostaglandin E compounds having uterine contractile activity, and preferably they are prostaglandin F and prostaglandin E analogues showing induction of menstruation, abortion or induction of labour by intravaginal administration, and more preferably 16,16-dimethyl-trans-$\Delta^2$-PGE$_1$ methyl ester (abbreviated ONO-802 hereafter).

The organic acids used in the drug-storing middle layers, may contribute to the stability of the prostaglandin analogues, and citric acid and tartaric acid are effective, and, therefore, preferred. The amount of the organic acid to be added is preferably such that it is added to the drug-storing middle layer at a proportion of 0.05–0.3% by weight.

Generally, PVP has poor plasticity, and is solid and brittle, but the addition of HPC and plasticizers at a suitable proportion gives it proper flexibility, and makes its plasticity easy. In order to improve its plasticity, for example, the addition of a proper amount of HPC—H and polyethylene glycol or lauryl alcohol as a plasticizer to Kollidon-90 is preferred. The total amount of HPC and the plasticizer to be added may be less than 50% by weight in the drug-storing middle layer.

The drug-storing middle layer may be obtained by dissolving one or more PVP, HPC and plasticizers in a proper organic solvent such as a lower alkanol, e.g. methanol or ethanol, or a mixture of a lower alkanol and acetone, etc., and, when a transparent solution is formed, adding a prostaglandin solution containing an organic acid dissolved in such an organic solvent as above mentioned, and after a homogeneous solution is formed, deaerating it sufficiently, and further drying by a conventional method to remove the organic solvent.

On the other hand, the release-controlling layers in the three-layered pharmaceutical film preparations of the present invention, are composed of one or more (a) HPC and (b) plasticizers. While the release-controlling layers most often do not contain any active ingredients, it is possible to incorporate a minor amount of the drug in them where it is necessary to release the drug in the earlier stage after administration.

The HPC used in the release-controlling layer, includes various standardized HPC mentioned above, alone or the combination of two or more of them, and HPC—H is more preferred in order to obtain the moderate release rate and the lastingness of the release.

The plasticizers used in the release-controlling layer, include various plasticizers mentioned above, alone or the combination of two or more of them, preferably propylene glycol or glycerol. The amount of the plasticizer to be added is preferably such that it is added to the release-controlling layer at a proportion of 5–15% by weight.

When various standardized HPC other than HPC—H is used as a base of the release-controlling layer, the release-controlling layer may be obtained by dissolving one or more HPC and plasticizers in a proper organic solvent such as a lower alkanol, e.g. methanol or ethanol, or a mixture of a lower alkanol and acetone etc., and, if desired, adding a prostaglandin solution containing an organic acid dissolved in such an organic solvent as above mentioned and, when a homogeneous solution is formed, deaerating it sufficiently, and further drying by a conventional method to remove the organic solvent.

It is previously pointed out that if the release-controlling layer composed of HPC—H is produced by the same procedure as mentioned for that composed of HPC other than HPC—H, various problems should occur. The present invention, furthermore, provides a new process for the production of the release-controlling layer composed of HPC—H having a suitable thickness by using a small amount of solvent. We have found that the release-controlling layer composed of HPC—H may be obtained most advantageously by utilizing the property that HPC—H may dissolve in water at a temperature below 40° C., but may not dissolve in it at a temperature more than 45° C. That is to say, the release-controlling layer composed of HPC—H may be obtained by adding one or more plasticizers, and HPC—H in hot water, preferably water warmed at 75°–80° C., suspending the mixture so as to homogeneously disperse, and if desired, adding a prostaglandin solution containing an organic acid dissolved in a small amount of an organic solvent such as a lower alkanol, e.g. methanol or ethanol, or a mixture of a lower alkanol and acetone etc., and spreading out the obtained suspension as a layer having the uniform thickness, and lowering its temperature below 45° C. to obtain a homogeneous solution layer owing to the swell of HPC—H, and raising its temperature to 60°–70° C. again to dry and remove water. By this method, the release-controlling layers which have no bubbles therein, and have flexibility and the desired thickness, may be easily obtained.

The three-layered pharmaceutical film preparations of the present invention may be obtained by mounting two release-controlling layers and one drug-storing middle layer obtained by the above methods, putting the drug-storing middle layer between two release-controlling layers, by a dry laminating method, e.g. by heating, or by a wet laminating method, e.g. by using a suitable organic solvent such as methanol or ethanol, or using a solution of HPC in a suitable organic solvent such as methanol or ethanol.

The three-layered pharmaceutical film preparations of the present invention are suitable for the administration to the mucosal tissue in the body cavity, particularly for intravaginal administration.

When the three-layered pharmaceutical film preparations of the present invention are administered to the mucosal tissue in the body cavity, they are swollen with the body liquid and expanded about ten times. Then the body liquid permeates into the drug-storing middle layer without decomposing the release-controlling layers and dissolves gradually the drug-storing middle layer, and the drug containing therein is leached out to show "zero-order release". Thereafter the release-controlling layers are dissolved gradually by the body liquid. Therefore, an ideal release pattern lasting for an extended period of time and high biological availability may be obtained.

In the three-layered pharmaceutical film preparations of the present invention, the release rate of the drug and the lasting time of the release suitable for the expected drug efficacy may be optionally established, (i) by changing the kind of HPC constituting the release-controlling layers or changing the constitutional ratio of HPC in the case where two or more of HPC are used, (ii) by changing the surface area and/or thickness of the release-controlling layers, (iii) by changing the kind of PVP and/or HPC constituting the drug-storing middle layer, or changing the constitutional ratio of them in the case where two or more of PVP or HPC are used, (iv) by changing the surface area and/or thickness of the drug-storing middle layer, (v) by changing the amount of the drug included in the drug-storing middle layer, and/or (vi) by incorporating the drug in the release-controlling layers.

The features of the three-layered pharmaceutical film preparations obtained according to the present invention are as follows:

(1) Since the drug is released passing through the release-controlling layer having little change of the surface area after swelling, the release is nearly a form of zero-order release and is most ideal release pattern.

(2) Since the biological availability is very high and hence a dosage level of the drug may be low, high effectiveness may be exhibited without the possibility of overdose.

(3) Since a constant release pattern of the drug is obtained regardless of the individuals, safer preparations may be obtained.

(4) Since the film preparations of the present invention apply to the administration to the body cavity and hence they are gradually dissolved by the body liquid after releasing the desired drug, the shape of the preparations does not remain and, therefore, there is unnecessary to remove it after use.

(5) During the film formation step, by addition of PVP, HPC, plasticizers and organic acids, unstable prostaglandin analogues are hardly decomposed and, therefore, the stability can be retained for an extended period of time.

(6) The release-controlling layers which have no bubbles therein, and have the uniform and desired thickness, may be easily prepared by suspending and dispersing HPC—H having high viscosity and high molecular weight in hot water at 75°–80° C., and then lowering its temperature below 45° C.

The size, shape, thickness etc. of the three-layered pharmaceutical film preparation of the present invention may be properly established depending on the pharmacological properties of the prostaglandin analogues contained therein, the purpose for use etc., and may be prepared using a conventional process for producing multi-layered film preparations.

The present invention is more fully described by the following examples and experimental example but the present invention should in no way be restricted thereto.

EXAMPLE 1

(a) Preparation of a release-controlling layer 15 g of propylene glycol were added to 240 ml of distilled water. The solution was fully warmed on water bath at 80° C., and thereto were added with stirring little by little 135 g of HPC—H previously sieved through a 200-mesh sieve, and then the mixture was stirred for about 15 minutes to obtain a suspension homogeneously dispersed. The suspension was quickly poured into and spread out in a tray which was previously warmed at 80° C. After lowering its temperature below 45° C., the homogeneous layer is changed into a homogeneous liquid layer by its swelling. The obtained liquid layer were fully dried in an oven at 60°–70° C. The film thus prepared was cut out to obtain about 1,000 sheets of the film being about 6.2 cm$^2$ in area and about 0.2 mm in thickness.

(b) Preparation of a drug-storing layer 118.3 g of Kollidon-90, 20 g of HPC—H, 20 g of polyethylene glycol 2000 (registered Trade Mark, prepared by Nippon Oils and Fats Co., Ltd.) and 40 g of polyethylene glycol 600 (registered Trade Mark, prepared by Nippon Oils and Fats Co., Ltd.) were, successively, dissolved in 1.9 liters of methanol with stirring at room temperature to obtain a homogeneous solution. To the solution, was added a solution of 1.5 g of ONO-802 and 0.2 g of citric acid in 100 ml of methanol and, thereafter, the solution was stirred fully and allowed to stand for effecting deaeration. The solution thus obtained was poured into a tray which was previously warmed at 40° C., with paying attention for babbles not to enter thereto, and dried in an oven. The film thus prepared was cut out to obtain about 1,000 sheets of the film being about 6.2 cm$^2$ in area and about 0.2 mm in thickness.

(c) Production of a three-layered film preparation

Two sheets of the film of the release-controlling layer obtained in the above (a) were laminated by heating with one sheet of the film of the drug-storing layer obtained in the above (b), placed therebetween to obtain a three-layered film preparation being about 0.7 mm in thickness.

EXAMPLE 2

(a) Preparation of a release-controlling layer

About 1,000 sheets of the film of the release-controlling layer, being about 0.3 mm in thickness and about 6.2 cm$^2$ in area were obtained similarly as Example 1 (a) by using 22.5 g of glycerol instead of propylene glycol employed in Example 1 (a), and 360 ml of distilled water and 202.5 g of HPC—H.

(b) Preparation of a drug-storing middle layer

About 1,000 sheets of the film of the drug-storing middle layer, being about 0.3 mm in thickness and about 6.2 cm$^2$ in area were obtained similarly as Example 1 (b) by using 60 g of lauryl alcohol instead of polyethylene glycol 2000 and polyethylene glycol 600 which were employed in Example 1 (b), using 0.6 g of tartaric acid instead of citric acid which was employed in Example 1 (b), and further using 2 liters of methanol, 117.9 g of Kollidon-90, 20 g of HPC—H and 1.5 g of ONO-802.

(c) Production of a three-layered film preparation

Two sheets of the film of the release-controlling layer obtained in the above (a) were laminated with a 2.5% solution of HPC in methanol, with one sheet of the film of the drug-storing middle layer obtained in the above (b), placed therebetween to obtain a three-layered film preparation being about 0.9 mm in thickness.

EXAMPLE 3

(a) Preparation of a release-controlling layer

About 1,000 sheets of the film of the release-controlling layer, being about 0.35 mm in thickness and about 6.2 cm$^2$ in area were obtained similarly as Example 1 (a) by using 416 ml of distilled water, 26 g of propylene glycol and 234 g of HPC—H.

(b) Production of a three-layered film preparation

Two sheets of the film of the release-controlling layer obtained in the above (a) were laminated with a 2.5% solution of HPC in methanol, with one sheet of the film of the drug-storing layer obtained in Example 1 (b), placed therebetween to obtain a three-layered film preparation being about 0.9 mm in thickness.

EXPERIMENTAL EXAMPLE

In order to compare the following preparations: the three-layered film preparation of the present invention, prepared in Example 1 and Example 3 (abbreviated L-HP film-(1) and L-HP film-(3), respectively, hereafter); a single-layered film preparation employing a water soluble polymer (prepared similarly as the description of Example 1 of the specification of Japanese Patent Kokai No. 56-34619, Derwent No. 37166D, using 199.5 mg of HPC—L, 0.2 mg of ONO-802 and 0.3 mg of citric acid; abbreviated HPC film hereafter); and a multi-layered film preparation employing a water soluble polymer and a water insoluble polymer (prepared similarly as the description of Example 1 of the specification of Japanese Patent Kokai No. 57-70816, Derwent No. 35619E, using 1.2 g of vinyl acetate resin, 2.4 g of HPC, 0.2 g of glycerol and 0.2 of triacetin for preparing drug release-controlling layers, and using 1.88 g of HPC, 10 mg of glycerol, 0.1 g of triacetin, 10 mg of ONO-802 and 3 mg of tartaric acid for preparing a drug-storing middle layer; abbreviated N-HP film hereafter), for the release rate of the drug and the long-lasting properties of the release, a dissolution test was conducted according to the modified USP paddle method (details of experiments are described hereafter). The results of the experiment are shown in Table 1 and the FIGURE.

Modified USP Paddle Method 700 ml of distilled water was placed in a flask and warmed at 37±0.5° C. 5-mesh wire net was settled at the bottom of the flask, and thereon a sheet of tested film preparation putting between two sheets of 60-mesh wire net was placed, and thereafter the solution in the flask was stirred at 25 r.p.m. At regular time intervals, 30 ml of the dissolution solution was withdrawn and 30 ml of distilled water previously warmed at 37±0.5° C. was added in the flask. To the dissolution solution withdrawn was added exactly 2 ml of internal standard solution (i.e. a 0.001% corticosterone acetate solution in acetonitrile). The solution was extracted with 10 ml of ethyl acetate twice (total:20 ml) and the extract was concentrated under reduced pressure. To the residue was added 0.1 ml of a 80% acetonitrile solution to use as HPLC (High Performance Liquid Chromatography) sample solution.

TABLE 1

| Sample | Percent Dissolution (%) in Various Preparations | | | | | | | | |
|---|---|---|---|---|---|---|---|---|---|
| | Dissolution Time (hr) | | | | | | | | |
| | ¼ | ½ | 1 | 2 | 3 | 4 | 6 | 8 | 10 | 12 |
| HPC film (Comparison) | 43 | 83 | | | | | | | | |
| N—HP film (Comparison) | | | | 28 | 58 | 69 | 74 | | | |
| L-HP film-(1) (Invention) | | | 4 | 12 | | 30 | 46 | 61 | 78 | 90 |
| L-HP film-(3) (Invention) | | | | | 15 | 21 | | 45 | | |

What is claimed is:

1. A three-layered pharmaceutical film preparation which comprises one drug-storing middle layer comprising at least one of each of (a) polyvinylprrolidone, (b) hydroxypropyl cellulose, (c) plasticizer, (d) organic acid and (e) prostaglandin analogue, and two release-controlling layers, one on each side of said middle layer, comprising at least one of each of (a) hydroxypropyl cellulose and (b) plasticizer, additionally containing or not containing at least one prostaglandin analogue.

2. A three-layered pharmaceutical film preparation according to claim 1, wherein the release-controlling layers do not contain prostaglandin analogues.

3. A three-layered pharmaceutical film preparation according to claim 1, wherein the release-controlling layers contain prostaglandin analogues.

4. A three-layered pharmaceutical film preparation according to claim 2 or 3, wherein the molecular weight of polyvinylpyrrolidone is 300,000–400,000.

5. A three-layered pharmaceutical film preparation according to claim 2 or 3, wherein the molecular weight of hydroxypropyl cellulose is 250,000–400,000.

6. A three-layered pharmaceutical film preparation according to claim 2 or 3, wherein the plasticizer is propylene glycol, glycerol, polyethylene glycol or lauryl alcohol.

7. A three-layered pharmaceutical film preparation according to claim 2 or 3, wherein the organic acid is citric acid or tartaric acid.

8. A three-layered pharmaceutical film preparation according to claim 2 or 3, wherein the prostaglandin analogue is a prostaglandin F compound or a prostaglandin E compound.

9. A three-layered pharmaceutical film preparation according to claim 2, wherein the drug-storing middle layer is composed of (a) polyvinylpyrrolidone having the molecular weight of 300,000–400,000, (b) hydroxypropyl cellulose having the molecular weight of 250,000–400,000, (c) polyethylene glycol, (d) citric acid and (e) 16,16-dimethyl-trans-$\Delta^2$-PGE$_1$ methyl ester, and the release-controlling layers are composed of (a) hydroxypropyl cellulose having the molecular weight of 250,000–400,000 and (b) propylene glycol.

10. A three-layered pharmaceutical film preparation according to claim 2, wherein the drug-storing middle layer is composed of (a) polyvinylpyrrolidone having the molecular weight of 300,000–400,000, (b) hydroxypropyl cellulose having the molecular weight of 250,000–400,000, (c) lauryl alcohol, (d) tartaric acid and (e) 16,16-dimethyl-trans-$\Delta^2$-PGE$_1$ methyl ester, and the release-controlling layers are composed of (a) hydroxypropyl cellulose having the molecular weight of 250,000–400,000 and (b) glycerol.

* * * * *